US008011905B2

(12) United States Patent
Artsyukhovich et al.

(10) Patent No.: US 8,011,905 B2
(45) Date of Patent: Sep. 6, 2011

(54) SURGICAL CASSETTE

(75) Inventors: Alexander N. Artsyukhovich, Laguna Niguel, CA (US); Mikhail Boukhny, Laguna Niguel, CA (US); Raphael Gordon, Ladera Ranch, CA (US); Gary P. Sorensen, Lake Forest, CA (US); David Thoe, Aliso Viejo, CA (US); Ralph E. Svetic, Costa Mesa, CA (US); Michael Yadlowsky, Irvine, CA (US)

(73) Assignee: Novartis AG, Basel (CH)

( * ) Notice: Subject to any disclaimer, the term of this patent is extended or adjusted under 35 U.S.C. 154(b) by 786 days.

(21) Appl. No.: 11/281,751

(22) Filed: Nov. 17, 2005

(65) Prior Publication Data

US 2007/0107490 A1    May 17, 2007

(51) Int. Cl.
*F04B 43/12* (2006.01)
*F04B 43/08* (2006.01)

(52) U.S. Cl. ..................... 417/477.2; 417/474

(58) Field of Classification Search ............. 73/1.16; 417/477.2; 604/30, 67, 151, 153, 189
See application file for complete search history.

(56) References Cited

U.S. PATENT DOCUMENTS

| | | | |
|---|---|---|---|
| 3,288,385 A | 11/1966 | Markakis et al. | |
| 3,615,155 A | 10/1971 | Gelbman | |
| 3,674,942 A | 7/1972 | Sugaya et al. | |
| 3,861,619 A | 1/1975 | Wolff | |
| 4,066,910 A | 1/1978 | Swift | |
| 4,187,057 A | 2/1980 | Xanthopoulos | |
| 4,385,958 A * | 5/1983 | Long | 156/361 |
| 4,395,258 A | 7/1983 | Wang et al. | |
| 4,399,332 A | 8/1983 | Furlan et al. | |
| 4,443,694 A | 4/1984 | Sanford | |
| 4,444,548 A | 4/1984 | Anderson et al. | |
| 4,475,904 A | 10/1984 | Wang | |
| 4,479,761 A | 10/1984 | Bilstad et al. | |
| 4,493,695 A | 1/1985 | Cook | |
| 4,526,515 A | 7/1985 | DeVries | |
| 4,537,561 A | 8/1985 | Xanthopoulos | |
| 4,550,247 A | 10/1985 | Winter et al. | |
| 4,623,776 A | 11/1986 | Buchroeder et al. | |
| 4,626,248 A | 12/1986 | Scheller | |
| 4,627,833 A | 12/1986 | Cook | |
| 4,712,907 A | 12/1987 | Weinberger et al. | |
| 4,713,051 A | 12/1987 | Steppe et al. | |
| 4,735,610 A | 4/1988 | Akkas et al. | |

(Continued)

FOREIGN PATENT DOCUMENTS

DE    20100591 U1    5/2001

(Continued)

OTHER PUBLICATIONS

Appleby, Julie, "Drug makers using spy-novel strategies to thwart knockoffs," Article, Aug. 19, 2003, 2 pgs., The Seattle Times.

(Continued)

*Primary Examiner* — Charles G Freay
*Assistant Examiner* — Alexander B Comley

(57) ABSTRACT

A surgical system and cassette, the cassette having an identification method that is specific to the cassette. Suitable methods include bar coding or Radio Frequency Identification ("RFID"). Cassette information that may be encoded include features such as lot number and performance characteristics, such as pressure sensor calibration data, flow and pressure data and any other performance characteristics of the cassette captured during testing of the cassette at manufacture.

22 Claims, 3 Drawing Sheets

U.S. PATENT DOCUMENTS

| | | | |
|---|---|---|---|
| 4,758,220 A | 7/1988 | Sundblom et al. | |
| 4,758,238 A | 7/1988 | Sundblom et al. | |
| 4,773,897 A | 9/1988 | Scheller et al. | |
| 4,790,816 A | 12/1988 | Sundblom et al. | |
| 4,798,580 A * | 1/1989 | DeMeo et al. | 604/30 |
| 4,798,850 A | 1/1989 | Brown | |
| 4,810,242 A | 3/1989 | Sundblom et al. | |
| 4,833,306 A | 5/1989 | Milbrett | |
| 4,837,857 A | 6/1989 | Scheller et al. | |
| 4,838,865 A | 6/1989 | Flank et al. | |
| 4,844,259 A | 7/1989 | Glowczewskie et al. | |
| 4,878,896 A * | 11/1989 | Garrison et al. | 604/65 |
| 4,963,131 A | 10/1990 | Wortrich | |
| 5,024,652 A | 6/1991 | Kohnke | |
| 5,041,096 A | 8/1991 | Beuchat et al. | |
| 5,048,870 A | 9/1991 | Mangini et al. | |
| 5,052,725 A | 10/1991 | Meyer et al. | |
| 5,085,492 A | 2/1992 | Kelane et al. | |
| 5,104,158 A | 4/1992 | Meyer et al. | |
| 5,106,366 A | 4/1992 | Steppe | |
| 5,163,900 A | 11/1992 | Wortrich | |
| 5,213,483 A * | 5/1993 | Flaherty et al. | 417/477.2 |
| 5,246,422 A | 9/1993 | Favre | |
| 5,267,956 A | 12/1993 | Beuchat | |
| 5,283,943 A | 2/1994 | Aguayo et al. | |
| 5,364,342 A | 11/1994 | Beuchat et al. | |
| 5,400,267 A | 3/1995 | Denen et al. | |
| 5,403,277 A | 4/1995 | Dodge et al. | |
| 5,408,076 A | 4/1995 | Griffanti | |
| 5,424,040 A | 6/1995 | Bjornsson | |
| 5,429,602 A | 7/1995 | Hauser | |
| 5,431,627 A * | 7/1995 | Pastrone et al. | 604/65 |
| 5,436,418 A | 7/1995 | Tamehira | |
| 5,460,490 A | 10/1995 | Carr et al. | |
| 5,475,571 A | 12/1995 | Dassanayake | |
| 5,488,223 A | 1/1996 | Austin et al. | |
| 5,494,074 A | 2/1996 | Ramacier, Jr. et al. | |
| 5,499,969 A | 3/1996 | Beuchat et al. | |
| 5,518,378 A | 5/1996 | Neftel et al. | |
| 5,531,697 A * | 7/1996 | Olsen et al. | 604/131 |
| 5,531,698 A * | 7/1996 | Olsen | 604/131 |
| 5,533,976 A | 7/1996 | Zaleski et al. | |
| 5,554,049 A | 9/1996 | Reynolds | |
| 5,588,815 A | 12/1996 | Zaleski, II | |
| 5,676,530 A | 10/1997 | Nazarifar | |
| 5,704,927 A | 1/1998 | Gillette et al. | |
| 5,724,244 A | 3/1998 | Yabuki | |
| 5,747,824 A | 5/1998 | Jung et al. | |
| 5,800,396 A | 9/1998 | Fanney et al. | |
| 5,845,264 A | 12/1998 | Nellhaus | |
| 5,899,674 A * | 5/1999 | Jung et al. | 417/477.2 |
| 5,908,027 A | 6/1999 | Butterfield et al. | |
| 5,911,403 A | 6/1999 | deCler et al. | |
| 5,920,054 A | 7/1999 | Uber, III | |
| 5,975,489 A | 11/1999 | deCler et al. | |
| 6,005,482 A | 12/1999 | Moran et al. | |
| 6,024,124 A | 2/2000 | Braun et al. | |
| 6,036,458 A | 3/2000 | Cole et al. | |
| 6,059,544 A * | 5/2000 | Jung et al. | 417/477.2 |
| 6,077,055 A * | 6/2000 | Vilks | 417/478 |
| 6,082,401 A | 7/2000 | Braun et al. | |
| 6,086,598 A * | 7/2000 | Appelbaum et al. | 606/107 |
| 6,098,892 A | 8/2000 | Peoples, Jr. | |
| 6,106,498 A * | 8/2000 | Friedli et al. | 604/153 |
| 6,110,110 A | 8/2000 | Dublin et al. | |
| 6,123,686 A * | 9/2000 | Olsen et al. | 604/151 |
| 6,155,975 A | 12/2000 | Urich et al. | |
| 6,161,578 A | 12/2000 | Braun et al. | |
| 6,172,609 B1 | 1/2001 | Lu et al. | |
| 6,204,491 B1 | 3/2001 | Montani | |
| 6,222,193 B1 | 4/2001 | Thurston et al. | |
| 6,231,089 B1 | 5/2001 | deCler et al. | |
| 6,238,623 B1 | 5/2001 | Amhof et al. | |
| 6,273,338 B1 | 8/2001 | White | |
| 6,319,031 B1 | 11/2001 | Greenstein | |
| 6,341,726 B1 | 1/2002 | Castanedo et al. | |
| 6,374,084 B1 | 4/2002 | Wilson | |
| 6,382,593 B1 | 5/2002 | deCler et al. | |
| 6,430,371 B1 | 8/2002 | Cho | |
| 6,468,241 B1 | 10/2002 | Gelfand et al. | |
| 6,519,569 B1 * | 2/2003 | White et al. | 705/3 |
| 6,574,166 B2 | 6/2003 | Niemiec | |
| 6,626,419 B2 | 9/2003 | deCler et al. | |
| 6,648,223 B2 | 11/2003 | Boukhny et al. | |
| 6,649,829 B2 | 11/2003 | Garber et al. | |
| 6,705,591 B2 | 3/2004 | deCler et al. | |
| 6,801,913 B2 | 10/2004 | Matsumura et al. | |
| 6,848,602 B2 | 2/2005 | deCler et al. | |
| 6,861,954 B2 | 3/2005 | Levin | |
| 6,868,720 B2 | 3/2005 | Lobdell et al. | |
| 6,897,374 B2 | 5/2005 | Garber et al. | |
| 6,899,476 B1 | 5/2005 | Barrus et al. | |
| 6,902,144 B2 | 6/2005 | deCler et al. | |
| 6,902,542 B2 * | 6/2005 | Gordon | 604/35 |
| 6,903,656 B1 | 6/2005 | Lee | |
| 6,916,007 B2 | 7/2005 | deCler et al. | |
| 6,917,291 B2 | 7/2005 | Allen | |
| 6,955,073 B2 | 10/2005 | Morgan et al. | |
| 6,978,800 B2 | 12/2005 | deCler et al. | |
| 7,236,936 B2 * | 6/2007 | White et al. | 705/3 |
| 7,268,684 B2 | 9/2007 | Tethrake et al. | |
| 7,273,483 B2 | 9/2007 | Wiener et al. | |
| 7,392,144 B2 | 6/2008 | Sorensen et al. | |
| 7,443,296 B2 | 10/2008 | Mezinsky et al. | |
| 7,484,769 B2 | 2/2009 | Domash et al. | |
| 7,568,619 B2 | 8/2009 | Todd et al. | |
| 7,796,040 B2 | 9/2010 | Mezhinsky et al. | |
| 2001/0006818 A1 | 7/2001 | Amhof et al. | |
| 2001/0020148 A1 | 9/2001 | Sasse et al. | |
| 2002/0017996 A1 | 2/2002 | Niemiec | |
| 2002/0032435 A1 | 3/2002 | Levin | |
| 2002/0143320 A1 | 10/2002 | Levin | |
| 2003/0127508 A1 | 7/2003 | Jones | |
| 2003/0178488 A1 | 9/2003 | Southard | |
| 2003/0178489 A1 | 9/2003 | Boukhny et al. | |
| 2003/0225363 A1 | 12/2003 | Gordon et al. | |
| 2004/0114879 A1 | 6/2004 | Hiereth et al. | |
| 2004/0116862 A1 * | 6/2004 | Ray | 604/151 |
| 2004/0220602 A1 | 11/2004 | Weng et al. | |
| 2005/0024588 A1 | 2/2005 | Lamm | |
| 2005/0118048 A1 * | 6/2005 | Traxinger | 417/477.2 |
| 2005/0277890 A1 * | 12/2005 | Stewart et al. | 604/189 |
| 2005/0285025 A1 | 12/2005 | Boukhny et al. | |
| 2006/0043177 A1 | 3/2006 | Nycz et al. | |
| 2006/0129140 A1 | 6/2006 | Todd et al. | |
| 2007/0005030 A1 | 1/2007 | Hopkins et al. | |
| 2007/0027459 A1 | 2/2007 | Horvath et al. | |
| 2007/0094303 A1 | 4/2007 | Zwingenberger et al. | |
| 2007/0098578 A1 | 5/2007 | Morgan | |
| 2007/0107490 A1 | 5/2007 | Artsyukhovich et al. | |
| 2007/0216526 A1 | 9/2007 | Volpi et al. | |
| 2007/0219494 A1 | 9/2007 | Gao et al. | |
| 2008/0020714 A1 | 1/2008 | Mezhinsky et al. | |
| 2008/0030343 A1 | 2/2008 | Raybuck et al. | |
| 2008/0054073 A1 | 3/2008 | Charles et al. | |
| 2008/0086279 A1 | 4/2008 | Svetic et al. | |
| 2008/0262654 A1 | 10/2008 | Omori et al. | |
| 2009/0121838 A1 | 5/2009 | Mezhinsky et al. | |

FOREIGN PATENT DOCUMENTS

| | | |
|---|---|---|
| EP | 0 320 168 | 7/1993 |
| EP | 550124 A2 | 7/1993 |
| EP | 550124 A3 | 7/1993 |
| EP | 0740370 B1 | 4/1996 |
| EP | 0740370 A1 | 10/1996 |
| EP | 550124 B1 | 5/2000 |
| EP | 0 776 670 B1 | 9/2001 |
| EP | 1199046 A2 | 4/2002 |
| EP | 1 366 775 A1 | 12/2003 |
| EP | 1410766 A1 | 4/2004 |
| EP | 1484899 A2 | 12/2004 |
| EP | 1199046 A3 | 1/2005 |
| EP | 1504714 A1 | 2/2005 |
| EP | 1484899 A3 | 3/2005 |
| EP | 1 366 775 B1 | 7/2005 |
| EP | 1504714 B1 | 2/2007 |
| EP | 1 787 606 A1 | 5/2007 |

| | | | |
|---|---|---|---|
| EP | 1199046 B1 | 6/2008 |
| EP | 1 787 606 B1 | 8/2008 |
| EP | 1410766 B1 | 5/2010 |
| JP | 409205291 A | 8/1997 |
| JP | 9282717 | 10/1997 |
| JP | H11-195991 | 7/1999 |
| JP | 2003-61975 A | 3/2003 |
| JP | 2003-61977 A | 3/2003 |
| JP | 2003-93401 A | 4/2003 |
| RU | 2212867 C2 | 9/2003 |
| SU | 1364333 A1 | 1/1988 |
| WO | WO 93/18802 | 9/1993 |
| WO | WO 95/28190 | 10/1995 |
| WO | WO 97/02059 | 1/1997 |
| WO | WO 99/17818 A | 4/1999 |
| WO | WO 01/14912 A1 | 3/2001 |
| WO | WO 02/34314 A | 5/2002 |
| WO | WO 02/099774 A2 | 12/2002 |
| WO | WO 02/099774 A3 | 12/2002 |
| WO | WO 03/013372 A2 | 2/2003 |
| WO | WO 03/026558 A2 | 4/2003 |
| WO | WO 03/013372 A3 | 9/2003 |
| WO | WO 03/081379 A2 | 10/2003 |
| WO | WO 03/081379 A3 | 10/2003 |
| WO | WO 03/026558 A3 | 12/2003 |
| WO | WO 2006/036600 A1 | 4/2006 |
| WO | WO 2006/066035 A2 | 6/2006 |
| WO | WO 2006/066035 A3 | 8/2006 |

OTHER PUBLICATIONS

Atmel Corporation, "Electronic Immobilizers for the Automotive Industry," Jun. 2003, 20 pgs., U2270B, Rev. 2661A-RFID.

Lee, Dr. Youbok, "MCRF, 355/360 Applications," 1999, 6 pgs., AN707, DS00707A, Microchip Technology, Inc.

Baschet-Vernet, Marion, "Smart packages may help control prescriptions," Journal, Nov. 2002, 4 pgs., No. 5, Pharmpack Europe.

Pharmpack Europe, [Special Compliance] "Labeling: Fitting Everything in," Nov. 2002, vol. 5, p. 31.

Chan, W.L., et al. Real Time Data Compression for Power System Monitoring Using Programmable Gate Array, Patent, 1993, 4 pgs., IEEE Tencon, Beijing.

Nygaard, Ranveig, "Signal Compression by Second Order Polynomials and Piecewise Non-Interpolating Approximation," Patent, 6 pgs. 1999.

Abstract of RU 27481 U1, Oct. 2, 2003.

Abstract of JP 20000217836A, Olympus Optical Co., Ltd., Aug. 8, 2000.

* cited by examiner

SURGICAL CASSETTE

BACKGROUND OF THE INVENTION

This invention relates generally to the field of surgical cassettes and more particularly to an identification system for surgical cassettes.

The use of cassettes with surgical instruments to help manage irrigation and aspiration flows into and out of a surgical site is well-known. See, for example, U.S. Pat. Nos. 4,493, 695, 4,627,833 (Cook), U.S. Pat. No. 4,395,258 (Wang, et al.), U.S. Pat. No. 4,713,051 (Steppe, et al.), U.S. Pat. No. 4,798,850 (DeMeo, et al.), U.S. Pat. Nos. 4,758,238, 4,790, 816 (Sundblom, et al.), U.S. Pat. Nos. 5,267,956, 5,364,342 (Beuchat), U.S. Pat. No. 6,036,458 (Cole, et al.) and U.S. Pat. No. 6,059,544 (Jung, et al.), the entire contents of which being incorporated herein by reference.

The fluidic performance of the surgical instrument is substantially affected by the fluidic performance of the cassette. As a result, current surgical instrumentation and cassettes are designed to work as an integral system, with the fluidic performance of the cassette designed to optimize the fluidic performance of the entire surgical system. Recent advances made in surgical instrumentation now allow the surgeon to manually or automatically control the operating parameters of the surgical instrumentation to a very fine degree. Specialized cassettes have been developed to allow the surgeon to capitalize on the advance control afforded by modern surgical instrumentation. The operating parameters of the surgical instrumentation, however, must be adjusted depending upon the cassette being used. One system, disclosed in U.S. Pat. No. 6,059,544 (Jung, et al.), has a cassette with a series of frangible tabs that can be used to allow the instrument to recognize the type of cassette being used. While such a system works very well, and has been commercially successful, the cassette identification system disclosed in this reference identifies only the type of cassette installed in the surgical console, and does not provide any information as to the performance characteristics of the specific cassette. Other ophthalmic surgical instruments contain embedded memory chips or other ID methods that allow the surgical console to recognize the instrument and adjust the console automatically to appropriate operating parameters. None of these systems; however, is capable of recognizing a specific cassette or instrument and adjusting the surgical console for the unique performance characteristics of a specific cassette or instrument.

Accordingly, a need exists for a cassette identification system that identifies the performance parameters for each specific cassette.

BRIEF SUMMARY OF THE INVENTION

The present invention improves upon the prior art by providing a surgical system and cassette, the cassette having an identification method that is specific to the cassette. Suitable methods include bar coding or Radio Frequency Identification ("RFID"). Cassette information that may be encoded include features such as lot number and performance characteristics, such as pressure sensor calibration data, flow and pressure data and any other performance characteristics of the cassette captured during testing of the cassette at manufacture.

Accordingly, one objective of the present invention is to provide a surgical cassette that can be readily identified by the surgical instrument in which the cassette is used.

Another objective of the present invention is to provide a surgical system that recognizes information that is cassette specific.

Still another objective of the present invention is to provide a cassette encoded with information specific to the cassette.

These and other advantages and objectives of the present invention will become apparent from the detailed description and claims that follow.

DETAILED DESCRIPTION OF THE PREFERRED EMBODIMENTS

Figure 1:
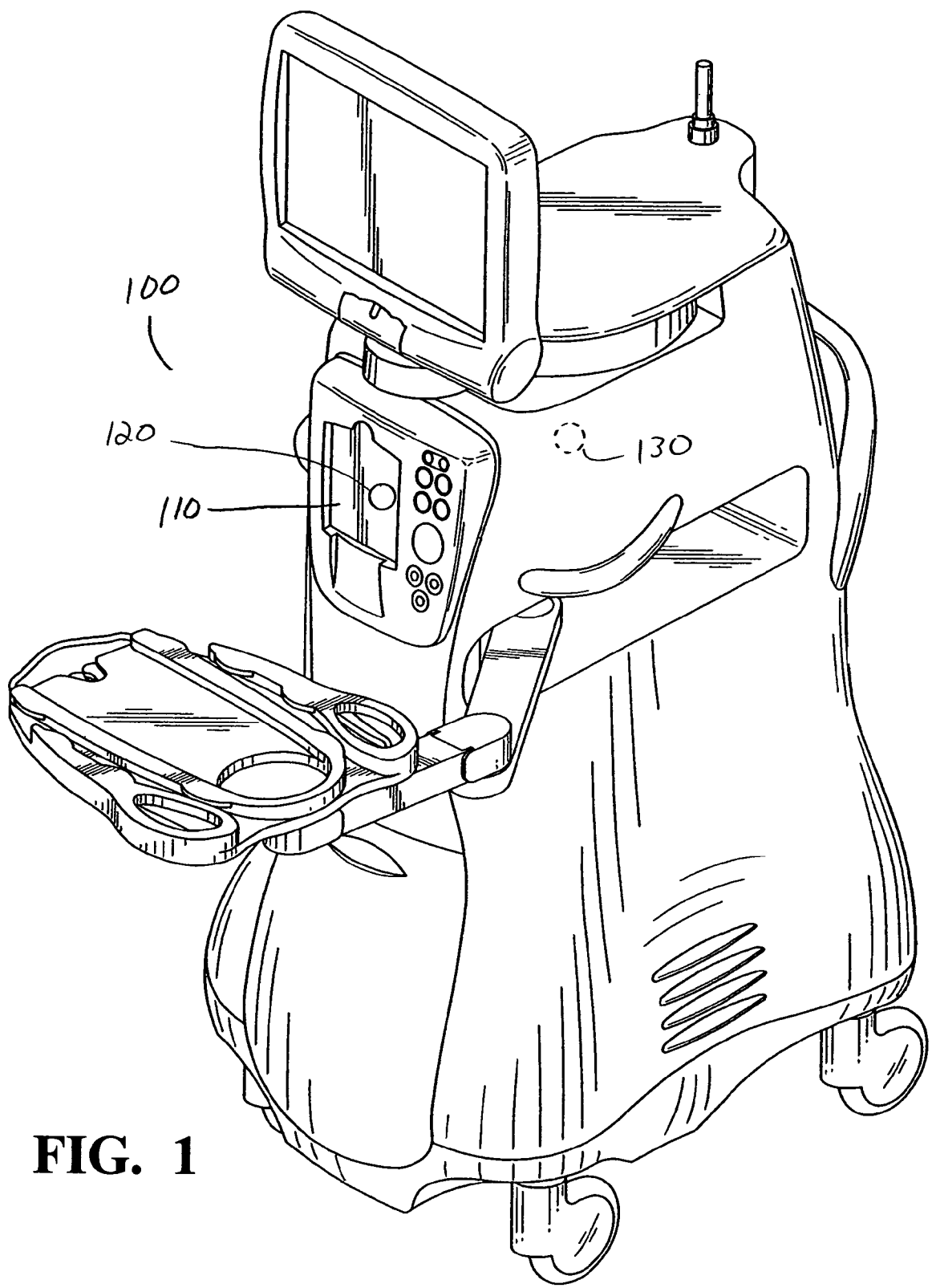
FIG. 1 is a perspective view of a surgical console that may be used with the system of the present invention.
Figure 2:
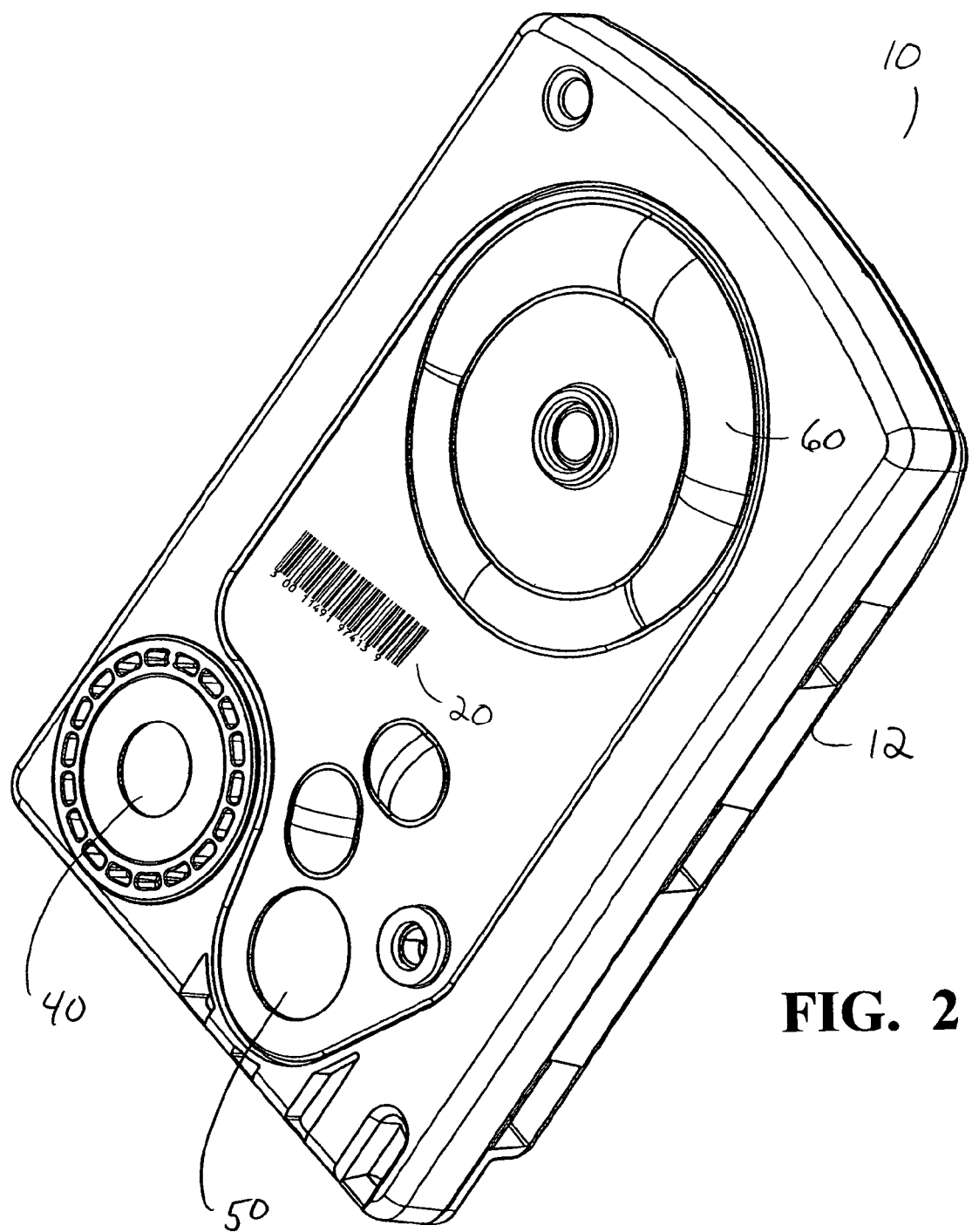
FIG. 2 is a perspective view of a first embodiment of a cassette suitable for use with the present invention.
Figure 3:
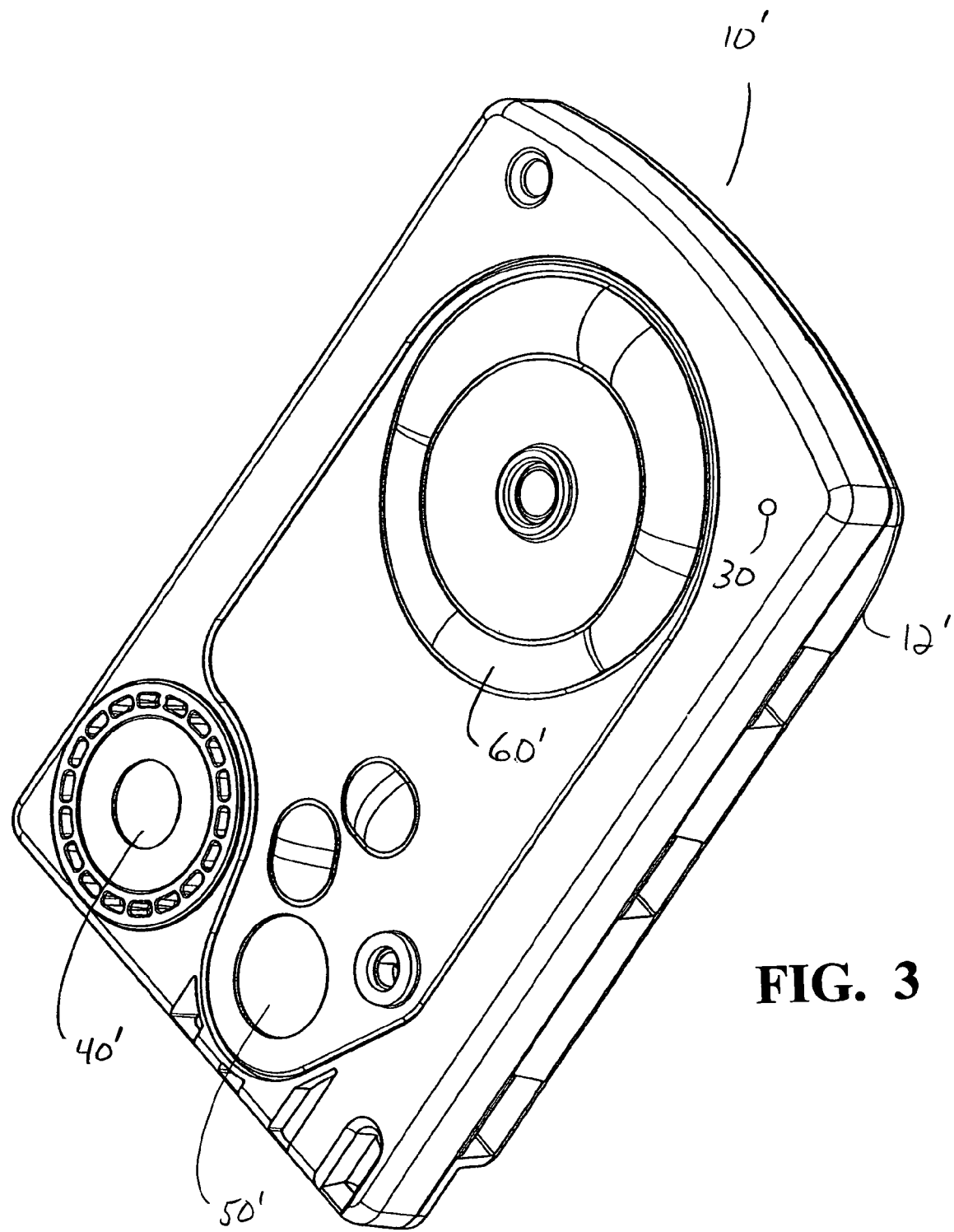
FIG. 3 is a perspective view of a first embodiment of a cassette suitable for use with the present invention.

As best seen in FIG. 1, surgical console 100 generally contains cassette receiving portion 110 that may contain reader 120. Console 100 may be any suitable surgical console, such as the INFINTI® Surgical System commercially available from Alcon Laboratories, Fort Worth, Tex. As best seen in FIG. 2, cassette 10 that may be used with the present invention generally contains bar code 20 placed in a location corresponding to optical reader 120 when cassette 10 is placed within cassette receiving portion 110 of console 100. One skilled in the art will recognize that reader 120 may be a bar code reader, a CCD camera, a CMOS sensor or other suitable optical reader. Bar code 20 may be printed on housing 12 in any suitable location and in any suitable color designed to perform optimally with reader 120. By way of example, bar code 20 may be printed on pressure sensor 40. In this way, if pressure sensor 40 is an optical pressure sensor, reader 120 can be used both for cassette 10 identification and as part of pressure sensor 40. Cassette 10 may be any suitable irrigation/aspiration cassette, such as the INFINTI® Fluid Management System commercially available from Alcon Laboratories, Fort Worth, Tex. Alternatively, as seen in FIG. 3, cassette 10' may contain, within or on housing 12', a non-optical means, such as an acoustic or a hard wired or wireless communication device, with microcomputer or RFID chip 30 being one specific example, that is read by detector or receiver 130 in console 100, appropriate microcomputer or RFID chips and detectors/receivers being well-known in the art.

During manufacture of cassettes 10 and 10', information specific to each individual cassette can be recorded into bar code 20 or chip 30. Such information can include lot number, manufacture date, component part tracking information and similar information about cassettes 10 and 10'. In addition, cassettes 10 and 10' may be tested during manufacture and the specific operating performance of individual cassettes 10 and 10' can be recorded and included in the information provided in bar code 20 or chip 30. Such information can include calibration data for aspiration pressure sensors 40 and 40', irrigation pressure sensors 50 and 50', the performance characteristics of peristaltic pump tubes 60 and 60', such characteristics possibly including vacuum rise time, maximum vacuum and flow resistance and being unique to each individual cassette 10 or 10'. Such information can be transferred to surgical console 100 through bar code 20 or chip 30 so that the software contained within console 100 can make automatically, appropriate adjustments in the operating parameters of console 100 to help assure optimum performance of surgical console 100 and cassettes 10 and 10'.

This description is given for purposes of illustration and explanation. It will be apparent to those skilled in the relevant art that changes and modifications may be made to the invention described above without departing from its scope or spirit.

We claim:

1. A surgical system, comprising:
    a surgical console having a cassette receiving portion;
    a cassette sized and shaped to be received in the cassette receiving portion of the surgical console, the cassette comprising:
        a housing;
        a pressure sensor coupled to the housing;
        a bar code, located on the cassette; and
        pressure sensor calibration data, stored in the bar code, that includes unique information specific to operation of the pressure sensor coupled to the housing and determined for that unique pressure sensor by testing that unique pressure sensor on the cassette at manufacture;
    wherein the surgical console comprises an optical reader configured to read the pressure sensor calibration data when the cassette is in the cassette receiving portion of the surgical console;
    wherein software contained within the console is configured to automatically make appropriate adjustments in operating parameters of the console, in response to the read pressure sensor calibration data; and
    wherein said pressure sensor calibration data for multiple cassettes are determined by testing the pressure sensor on each cassette at manufacture.

2. The system of claim 1, wherein the console is configured to automatically make appropriate adjustments in the operating parameters of the console, in response to reading said pressure sensor calibration data, to help assure optimum performance of the surgical console in combination with an individual cassette.

3. A surgical cassette sized and shaped to be received in a cassette receiving portion of a surgical console, the cassette comprising:
    a housing;
    a pressure sensor coupled to the housing;
    a bar code, located on the cassette; and
    pressure sensor calibration data, stored in the bar code, that includes unique information specific to operation of the pressure sensor and determined for the pressure sensor by testing the pressure sensor on the cassette at manufacture;
    wherein the surgical console has an optical reader configured to read pressure sensor calibration data within the bar code when the cassette is in the cassette receiving portion of the surgical console; and
    wherein said pressure sensor calibration data for multiple cassettes are determined by testing the pressure sensor on each cassette at manufacture.

4. The cassette of claim 3, wherein the bar code additionally includes individual cassette identification data, including lot number, manufacture date, and/or component part tracking information.

5. The surgical cassette of claim 3, wherein the pressure sensor is an aspiration pressure sensor and wherein said pressure sensor calibration data includes calibration data for the aspiration pressure sensor.

6. The surgical cassette of claim 5, wherein the pressure sensor is on an exterior of the housing.

7. The system of claim 1, wherein the pressure sensor is an irrigation pressure sensor and wherein said pressure sensor calibration data includes calibration data for the irrigation pressure sensor.

8. The surgical cassette of claim 3, wherein the pressure sensor is an irrigation pressure sensor and wherein said pressure sensor calibration data includes calibration data for the irrigation pressure sensor.

9. A method of manufacturing surgical cassettes, comprising:
    providing a housing for each cassette;
    coupling a separate pressure sensor to each of the cassette housings;
    determining pressure sensor calibration data individually for each separate pressure sensor by individually testing each separate pressure sensor during manufacturing; and
    coupling a bar code, with unique determined pressure sensor calibration data for a specific pressure sensor, to the cassette housing coupled to that specific pressure sensor;
    wherein the cassette is configured to be received in a surgical console that includes an optical reader configured to read the pressure sensor calibration data contained within the bar code when the cassette is received in the surgical console to automatically make appropriate adjustments in the operating parameters of the console according to the pressure sensor calibration data for that one unique pressure sensor.

10. The method of claim 9, further comprising storing encoded individual cassette identification data on the bar code.

11. The system of claim 1, wherein the bar code additionally includes individual cassette identification data including lot number, manufacture date, and/or component part tracking information.

12. The system of claim 1, wherein the pressure sensor is an aspiration pressure sensor and wherein said pressure sensor calibration data includes calibration data for the aspiration pressure sensor.

13. The system of claim 1, wherein the bar code is at least partially printed on the pressure sensor.

14. The cassette of claim 3, wherein the bar code is at least partially printed on the pressure sensor.

15. The method of claim 9, wherein the determined pressure sensor calibration data for the pressure sensor includes unique information specific to operation of that unique pressure sensor determined for that one unique pressure sensor by testing that one unique pressure sensor at manufacture.

16. The method of claim 9, wherein at least one pressure sensor is an aspiration pressure sensor.

17. The method of claim 9, wherein at least one pressure sensor is an irrigation pressure sensor.

18. The method of claim 9, wherein the bar code further comprises individual cassette identification data including lot number, manufacture date, and/or component part tracking information.

19. The system of claim 1, wherein the optical reader is a bar code reader, a CCD (Charge-Coupled Device) camera, or a CMOS (Complementary Metal-Oxide Semiconductor) sensor.

20. The method of claim 9, wherein a first bar code coupled to a first cassette of the cassette housings includes different pressure sensor calibration data than a second bar code coupled to a second cassette of the cassette housings and wherein the first cassette and the second cassette are coupled to a same type of pressure sensor and wherein the different pressure sensor calibration data reflects calibration differences between the same type pressure sensors.

21. The surgical system of claim 1, wherein said pressure sensor calibration data for multiple cassettes are determined by testing at least two pressure sensors on each cassette at manufacture.

22. The surgical system of claim 3, wherein said pressure sensor calibration data for multiple cassettes are determined by testing at least two pressure sensors on each cassette at manufacture.

* * * * *